(12) United States Patent
Allsop (10) Patent No.: US 10,272,213 B2
(45) Date of Patent: Apr. 30, 2019

(54) FLUID DELIVERY DEVICE

(71) Applicant: CONSORT MEDICAL PLC, Hertfordshire (GB)

(72) Inventor: Paul Allsop, Norfolk (GB)

(73) Assignee: CONSORT MEDICAL PLC, Hemel Hempstead, Hertfordshire (GB)

( * ) Notice: Subject to any disclaimer, the term of this patent is extended or adjusted under 35 U.S.C. 154(b) by 701 days.

(21) Appl. No.: 14/904,376

(22) PCT Filed: Jul. 14, 2014

(86) PCT No.: PCT/GB2014/052141
§ 371 (c)(1),
(2) Date: Jan. 11, 2016

(87) PCT Pub. No.: WO2015/008048
PCT Pub. Date: Jan. 22, 2015

(65) Prior Publication Data
US 2016/0166780 A1 Jun. 16, 2016

(30) Foreign Application Priority Data

Jul. 19, 2013 (GB) .................................. 1312980.4

(51) Int. Cl.
*A61M 11/00* (2006.01)
*A61M 15/00* (2006.01)
(Continued)

(52) U.S. Cl.
CPC ......... *A61M 11/007* (2014.02); *A61F 9/0008* (2013.01); *A61M 15/0091* (2013.01);
(Continued)

(58) Field of Classification Search
CPC ............. A61M 11/007; A61M 15/0028; B05B 11/3004; B05B 11/3052; B05B 11/3059; B05B 11/3091; B05B 11/3092
(Continued)

(56) References Cited

U.S. PATENT DOCUMENTS 4,079,862 A 3/1978 Fegley
4,394,934 A 7/1983 Fegley
(Continued)

FOREIGN PATENT DOCUMENTS

CN 1287890 A 3/2001
CN 1355731 A 6/2002
(Continued)

OTHER PUBLICATIONS

Search Report from UK Intellectual Property Office for GB Application No. GB1312980.4 dated Dec. 31, 2013. (4 pages).
(Continued)

*Primary Examiner* — Nathan R Price
*Assistant Examiner* — John A Doubrava
(74) *Attorney, Agent, or Firm* — Smith, Gambrell & Russell, LLP (57) ABSTRACT

Fluid delivery device for discharging a fluid, having: a housing; piston pump; biasing mechanism; and trigger mechanism. The housing has a basal end and a discharge end with outlet for discharging the fluid. The piston pump has a casing defining a pump chamber for storage of fluid, a piston slidably movable relative to the pump chamber, a piston plunger, and a delivery channel. The trigger mechanism is movable from a cocked configuration wherein the trigger mechanism prevents transfer of a biasing force of the biasing mechanism to the casing to a triggered configuration with the trigger mechanism enabling transfer of the biasing force to the casing to cause movement of the casing towards the
(Continued)

housing outlet to discharge fluid from the pump chamber, along the delivery channel and out of the outlet of the housing. The biasing mechanism has one or more flexible catch members and a manually operable trigger.

20 Claims, 9 Drawing Sheets (51) Int. Cl.
 A61M 15/08 (2006.01)
 B05B 11/00 (2006.01)
 A61F 9/00 (2006.01)
(52) U.S. Cl.
 CPC ........... *A61M 15/08* (2013.01); *B05B 11/007* (2013.01); *B05B 11/3001* (2013.01); *B05B 11/3004* (2013.01); *B05B 11/3052* (2013.01); *B05B 11/3059* (2013.01); *B05B 11/3091* (2013.01); *A61M 2205/42* (2013.01); *A61M 2205/582* (2013.01); *A61M 2205/583* (2013.01); *A61M 2210/0618* (2013.01)
(58) Field of Classification Search
 USPC ................ 604/192, 325; 128/200.14, 20.22, 128/203.21, 203.12; 222/153.13, 321.6, 222/386, 340, 336, 319
 See application file for complete search history.

(56) References Cited

U.S. PATENT DOCUMENTS

| | | | |
|---|---|---|---|
| 5,289,818 A | 3/1994 | Citterio et al. | |
| 5,431,155 A | 7/1995 | Marelli | |
| D384,881 S | 10/1997 | Uhl et al. | |
| D414,261 S | 9/1999 | Ritsche | |
| 6,059,150 A | 5/2000 | Fuchs et al. | |
| 6,401,987 B1 | 6/2002 | Oeschsel et al. | |
| 6,427,878 B1 | 8/2002 | Greiner-Perth et al. | |
| 6,708,846 B1 | 3/2004 | Fuchs et al. | |
| D504,068 S | 4/2005 | Thuillier et al. | |
| D518,730 S | 4/2006 | Caserta et al. | |
| D526,902 S | 8/2006 | Cummings | |
| D535,022 S | 1/2007 | Davies | |
| D544,956 S | 6/2007 | Collins et al. | |
| 7,258,119 B2 | 8/2007 | Mazonni | |
| 7,302,948 B2 | 12/2007 | Anderson | |
| D573,251 S | 7/2008 | Pentafragas | |
| 7,699,052 B2 | 4/2010 | Schiewe et al. | |
| 7,731,065 B2 | 6/2010 | Ingram et al. | |
| 8,210,167 B2 | 7/2012 | Corbacho | |
| 8,348,096 B2 | 1/2013 | Greiner-Perth | |
| D686,312 S | 7/2013 | Allsop | |
| 8,590,750 B2 | 11/2013 | Warby | |
| 9,314,808 B2* | 4/2016 | Allsop .................. A61M 11/00 |
| 2001/0056259 A1 | 12/2001 | Skinkle et al. | |
| 2004/0153033 A1 | 8/2004 | Mazzoni | |
| 2005/0098172 A1* | 5/2005 | Anderson ............. A61M 15/08 |
| | | | 128/200.23 |
| 2006/0016833 A1* | 1/2006 | Greiner-Perth ..... B05B 11/3052 |
| | | | 222/383.1 |
| 2008/0210228 A1 | 9/2008 | Corbacho | |
| 2010/0095957 A1 | 4/2010 | Corbacho | |
| 2010/0145275 A1 | 6/2010 | Grunhut et al. | |
| 2014/0231457 A1 | 8/2014 | Allsop | |

FOREIGN PATENT DOCUMENTS

| | | |
|---|---|---|
| DE | 102012203866 | 9/2012 |
| EM | 001836941-0001 | 3/2011 |
| EP | 1219356 | 7/2007 |
| FR | 2682305 | 4/1993 |
| GB | 2489216 | 9/2012 |
| GB | 2495576 | 10/2013 |
| WO | 92/20455 | 11/1992 |
| WO | 98/12511 | 3/1998 |
| WO | 02/083218 | 10/2002 |
| WO | 03/074189 | 9/2003 |
| WO | 2004/069664 | 8/2004 |
| WO | 2010/037759 A1 | 4/2010 |
| WO | 2013/054076 | 4/2013 |
| WO | 2015/008048 | 1/2015 |

OTHER PUBLICATIONS

Examination Report from UK Intellectual Property Office for GB Application No. GB1312980.4 dated Jul. 8, 2015. (1 page).
International Preliminary Report on Patentability for PCT/GB2012/000778 dated Apr. 15, 2014.
International Search Report and Written Opinion for PCT/GB2012/000778, dated Feb. 6, 2013.
Great Britain Search Report issued from Intellectual Property Office, in Application No. GB 1117518.9, dated Jan. 27, 2012.
International Search Report and Written Opinion for PCT/GB2014/052141, dated Jan. 22, 2015.

* cited by examiner

FLUID DELIVERY DEVICE

The present disclosure relates to a fluid delivery device. In particular, it relates to a fluid delivery device for nasal, sub-lingual or ophthalmic use.

Fluid delivery devices are well known for dispensing media such as powders and fluids for discharge into or onto the body. EP1219356 discloses one such device in which a piston pump is used for discharging a flowable media from a reservoir out of an outlet nozzle for nasal delivery. To operate the device a user manually displaces upwardly the reservoir relative to a support surface to cause a needle to form an opening in a sealing piston of the reservoir. Further manual movement of the reservoir by the user displaces the piston within the reservoir to pressurise the flowable media and cause it to be discharged via the needle.

WO2004/069664 discloses a closure member suitable for use in fluid delivery devices having a piston pump. The closure member does not require piercing by a needle. Instead one or more resilient projections on the closure member are used to seal a storage container. On actuation manual displacement of the closure member relative to the storage container causes the one or more resilient projections to deform accommodating outflow of fluid from the storage container.

In both cases the devices rely on manual displacement of at least one part of the piston pump for operation. This can lead to inconsistent discharge of media from the devices. Reasons include the different impulses and loads applied to the piston pump by different users and the possibility that a user will not fully complete the required stroke of the piston pump before releasing the device.

WO2013/054076, by the present applicant, describes a fluid delivery device for discharging a fluid comprising:
  a housing;
  a piston pump;
  a biasing mechanism; and
  a trigger mechanism;
  the housing comprising a basal end and a discharge end having an outlet for discharging the fluid;
  the piston pump comprising a casing defining a pump chamber for storage of the fluid, a piston slidably movable relative to the pump chamber, a piston plunger, and a delivery channel for delivering fluid discharged from the pump chamber to the outlet of the housing;
  the trigger mechanism being movable from a cocked configuration to a triggered configuration;
  in the cocked configuration the trigger mechanism prevents transfer of a biasing force of the biasing mechanism to the casing to thereby prevent movement of the casing towards the outlet of the housing;
  in the triggered configuration the trigger mechanism enables transfer of the biasing force to the casing to thereby cause movement of the casing towards the outlet of the housing so as to discharge fluid from the pump chamber, along the delivery channel and out of the outlet of the housing;
  characterised in that the biasing mechanism comprises one or more flexible catch members which in the cocked configuration are catched to the housing and in the triggered configuration are decoupled from the housing; and wherein the trigger mechanism comprises a manually movable button located at the basal end of the housing, the button comprising an obstructer that in the cocked configuration engages the one or more flexible catch members to prevent decoupling of the one or more catch members from the housing.

Advantageously, the operation of the fluid delivery device is simple and consistent. The use of the trigger mechanism in combination with the biasing mechanism results in a predictable loading and impulse being applied to the casing of the piston pump. In addition, the device ensures that the piston pump undergoes a full discharge stroke under the action of the biasing mechanism. As such, partial discharges are prevented.

The device of the present disclosure seeks to improve the known device of WO2013/054076.

The present disclosure provides a fluid delivery device for discharging a fluid comprising:
  a housing;
  a piston pump;
  a biasing mechanism; and
  a trigger mechanism;
  the housing comprising a basal end and a discharge end having an outlet for discharging the fluid;
  the piston pump comprising a casing defining a pump chamber for storage of the fluid, a piston slidably movable relative to the pump chamber, a piston plunger, and a delivery channel for delivering fluid discharged from the pump chamber to the outlet of the housing;
  the trigger mechanism being movable from a cocked configuration to a triggered configuration;
  in the cocked configuration the trigger mechanism prevents transfer of a biasing force of the biasing mechanism to the casing to thereby prevent movement of the casing towards the outlet of the housing;
  in the triggered configuration the trigger mechanism enables transfer of the biasing force to the casing to thereby cause movement of the casing towards the outlet of the housing so as to discharge fluid from the pump chamber, along the delivery channel and out of the outlet of the housing;
  the biasing mechanism comprising one or more flexible catch members which in the cocked configuration are catched to the housing and in the triggered configuration are decoupled from the housing; and wherein the trigger mechanism comprises a manually operable trigger located at the basal end of the housing, the manually operable trigger comprising a shroud and a slidable button;
  the slidable button comprising an obstructer that in the cocked configuration engages the one or more flexible catch members to prevent decoupling of the one or more catch members from the housing;
  wherein in the cocked configuration the slidable button projects outside the shroud so as to be accessible, and wherein in the triggered configuration the slidable button is retained within the shroud to provide a visual and tactile activation indicator.

The shroud may comprise a cup-shaped body having an outer lateral side wall and a concave lower end.

The shroud may further comprise an inner tubular section extending upwardly from the concave lower end to define a central conduit extending upwardly from an aperture in the concave lower end.

An upper end of the outer lateral side wall may comprise projections which engage with the housing to retain the shroud with respect to the housing.

The slidable button may comprise a concave lower face.

Preferably the slidable button is movable along a longitudinal axis of the device between the cocked and triggered configurations.

Preferably the biasing mechanism comprises a spring biasing the one or more catch members towards the triggered configuration.

Preferably the one or more catch members and the housing comprise inter-engaging surfaces that in the cocked configuration urge the catch members to flex and decouple from the housing, wherein the position of obstructer in the cocked configuration prevents said flexure.

The inter-engaging surfaces may comprise inclined surfaces on the catch members. The inclined surfaces may comprise one or more chamfers or radiused corners of the catch members.

Preferably the slidable button comprises an inwardly directed projection comprising an enlarged head at a distal end, wherein the enlarged head comprises the obstructer.

The one or more flexible catch members may comprises a plurality of flexible legs depending from a body portion, each flexible leg comprising a catch portion at a distal end. In which case, in the cocked configuration the catch portions may be located around the enlarged head of the obstructor and axially aligned therewith.

The slidable button may comprise, or be coupled to, a waisted section below the obstructer and the slidable button may be movable into the triggered configuration by movement away from the basal end into the housing so as to slide the enlarged head of the obstructor within the flexible legs to bring the waisted section into alignment with the catch portions. The waisted section may be integrally formed with a remainder of the obstructor and simply comprise a portion of the obstructor of reduced external diameter.

It is desirable to form the obstructor from a relatively stiff material such as polypropylene that is adequately able to resist the inwardly-directed force applied by the one or more catch members.

The slide member may comprise the one or more flexible catch members. Alternatively, the one or more flexible catch members may be integrally formed with the casing.

The slide member may comprise a recess for receiving and, optionally, abutting against the casing.

Preferably the piston comprises a body and at least one resilient projection to seal the pump chamber in the cocked configuration; wherein on movement of the casing towards the outlet of the housing in the triggered configuration, the at least one resilient projection is deflectable due to the resultant increase in pressure within the pump chamber so as to accommodate discharge of fluid from the pump chamber into the delivery channel.

Preferably the at least one resilient projection extends around only a portion of a circumference of the piston.

Preferably at least one sealing projection axially aligned with the at least one resilient projection extends round a remainder of the circumference of the piston.

In one embodiment the slide member may be configured, in the triggered configuration, to transfer the biasing force to the casing of the piston pump. The slide member may transfer the biasing force to the casing by direct contact therebetween.

In another embodiment the obstructor may be configured, in the triggered configuration, to transfer the biasing force to the casing of the piston pump. The obstructor may transfer the biasing force to the casing by direct contact therebetween.

In the cocked configuration one or more assembly gaps may be present between components of the device, for example, the piston plunger and the piston, wherein the obstructor may be configured to be of a sufficient length such that, starting from the cocked configuration, initial movement of the slidable button may cause the obstructor to contact and displace the casing and piston to close any said assembly gaps, prior to decoupling of the one or more catch members from the housing. This is advantageous in further reducing the operating noise of the device. It has been found that, where the force is transferred to the casing via a separate slide member, the presence of assembly gap(s) in the device can lead to impact noises during triggering as, for example, the piston plunger and piston are rapidly brought into contact with each other under the biasing force. By using the obstructor itself to transfer the forces, the assembly gap(s) may be closed relatively slowly during the manual movement of the button (including the obstructor) as the obstructor itself can bring all of the components into face-to-face contact before the release of the one or more catch members transfers the biasing force to the casing of the piston pump.

The piston and the piston plunger may be fixed relative to the housing.

The device may be a single-use device.

There is also provided a fluid delivery device as described above combined with a single dose of fluid contained in the pump chamber. The fluid may contain a pharmaceutical.

The term pharmaceutical, as used herein, is intended to encompass any pharmaceutical, compound, composition, medicament, agent or product which can be delivered or administered to a human being or animal, for example pharmaceuticals, drugs, biological and medicinal products. Examples include antiallergics, analgesics, bronchodilators, antihistamines, therapeutic proteins and peptides, antitussives, anginal preparations, antibiotics, anti-inflammatory preparations, hormones, or sulfonamides, such as, for example, a vasoconstrictive amine, an enzyme, an alkaloid, or a steroid, including combinations of two or more thereof. In particular, examples include isoproterenol [alpha-(isopropylaminomethyl)protocatechuyl alcohol], phenylephrine, phenylpropanolamine, glucagon, adrenochrome, trypsin, epinephrine, ephedrine, narcotine, codeine, atropine, heparin, morphine, dihydromorphinone, ergotamine, scopolamine, methapyrilene, cyanocobalamin, terbutaline, rimiterol, salbutamol, ipratropium bromide and salbutamol, flunisolide, colchicine, pirbuterol, beclomethasone, orciprenaline, fentanyl, and diamorphine, streptomycin, penicillin, procaine penicillin, tetracycline, chlorotetracycline and hydroxytetracycline, adrenocorticotropic hormone and adrenocortical hormones, such as cortisone, hydrocortisone, hydrocortisone acetate and prednisolone, insulin, cromolyn sodium, and mometasone, including combinations of two or more thereof.

The pharmaceutical may be used as either the free base or as one or more salts conventional in the art, such as, for example, acetate, benzenesulphonate, benzoate, bicarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate, (embonate), pantothenate, phosphate, diphosphate, polygalacturonate, salicylate, stearate, subacetate, succinate, sulphate, tannate, tartrate, and triethiodide, including combinations of two or more thereof. Cationic salts may also be used, for example the alkali metals, e.g. Na and K, and ammonium salts and salts of amines known in the art to be pharmaceutically acceptable, for example glycine, ethylene diamine, choline, diethanolamine, triethanolamine, octadecylamine, diethylamine, triethylamine, 1-amino-2-propanol-amino-2-(hydroxymethyl)propane-1,3-diol, and 1-(3,4-dihydroxyphenyl)-2 isopropylaminoethanol.

The pharmaceutical will typically be one which is suitable for nasal inhalation and may be provided in any suitable fluid form for this purpose, for example as a solution or powder suspension in a solvent or carrier liquid, for example ethanol, or isopropyl alcohol. The pharmaceutical may alternatively be one suitable for sub-lingual or ophthalmic delivery.

The pharmaceutical may, for example, be one which is suitable for the treatment of asthma. Examples include salbutamol, beclomethasone, salmeterol, fluticasone, formoterol, terbutaline, sodium chromoglycate, budesonide and flunisolide, and physiologically acceptable salts (for example salbutamol sulphate, salmeterol xinafoate, fluticasone propionate, beclomethasone dipropionate, and terbutaline sulphate), solvates and esters, including combinations of two or more thereof. Individual isomers such as, for example, R-salbutamol, may also be used. The pharmaceutical may, for example, be one which is suitable for the treatment of migraine. An example is sumatriptan. As will be appreciated, the pharmaceutical may comprise of one or more active ingredients, an example of which is flutiform. One or more surfactants may be included if desired.

The piston may be formed from an elastomer or thermoelastomer material such as EPDM, polychloroprene, hydrogenated nitrile, butyl, halo-butyl, dynamically cross-linked EPDM/PP (Santoprene®), styrenic block copolymers or blends thereof. Other suitable materials include high-density polyethylene and low-density polyethylene The housing may be formed from an engineering plastic such as polypropylene, HDPE, ABS, polyester or POM.

The casing of the piston pump may be formed from any suitable material such as glass, cyclic olefin copolymer—an example being Topas® COC available from TOPAS Advanced Polymers GmbH, Frankfurt-Höchst, Germany, or liquid crystal polymer—an example being Zenite® LCP available from DuPont, Wilmington, USA.

Components of the biasing mechanism, trigger mechanism and housing may be formed from a suitable material having the necessary flexural characteristics, such as polypropylene, HDPE, ABS, polyester or POM.

The present disclosure will now be described, by way of example only, with reference to the accompanying drawings in which.

In the following, the fluid delivery device will be described, by way of example only, as a device suitable for nasal delivery of fluid.

In the following, the first, second and third devices of FIGS. 1 to 8 are known devices from the applicant's International application, WO2013/054076 and are described by way of background information.

As shown in the accompanying FIGS. 1 to 6, the first nasal device 1 comprises an upper housing 2, a lower housing 3, a piston pump 4, a spring 5 and a trigger mechanism 6.

Figure 1:
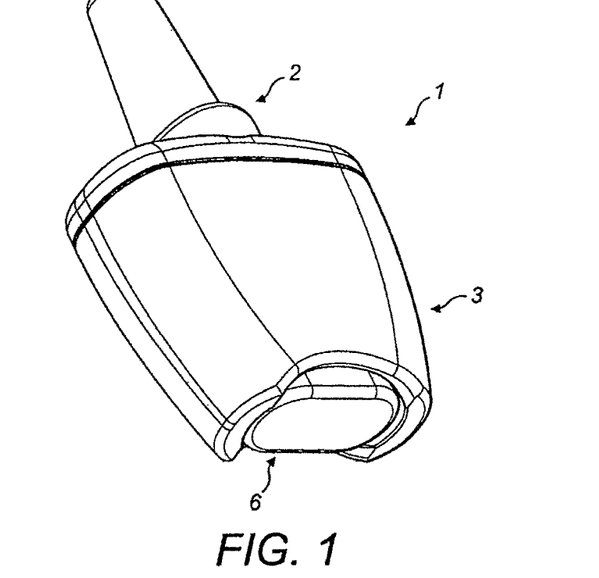
FIG. 1 is a perspective view of a first nasal device as described in WO2013/054076.
Figure 2:
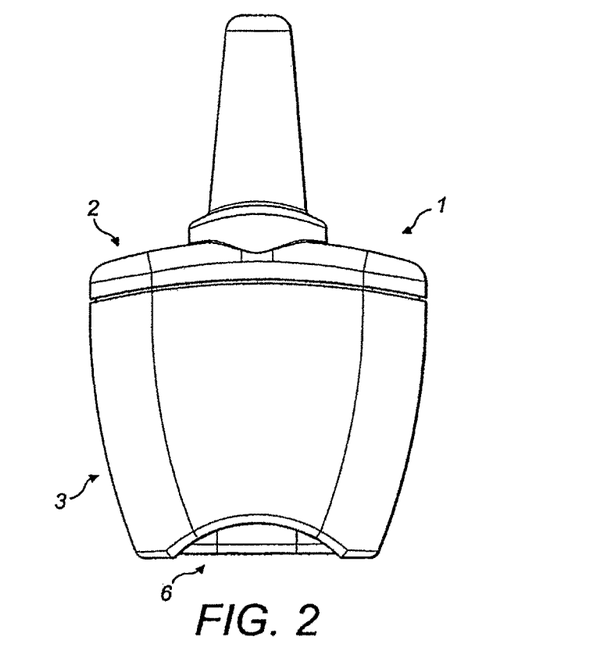
FIG. 2 is a side elevation of the nasal device of FIG. 1.
Figure 3:
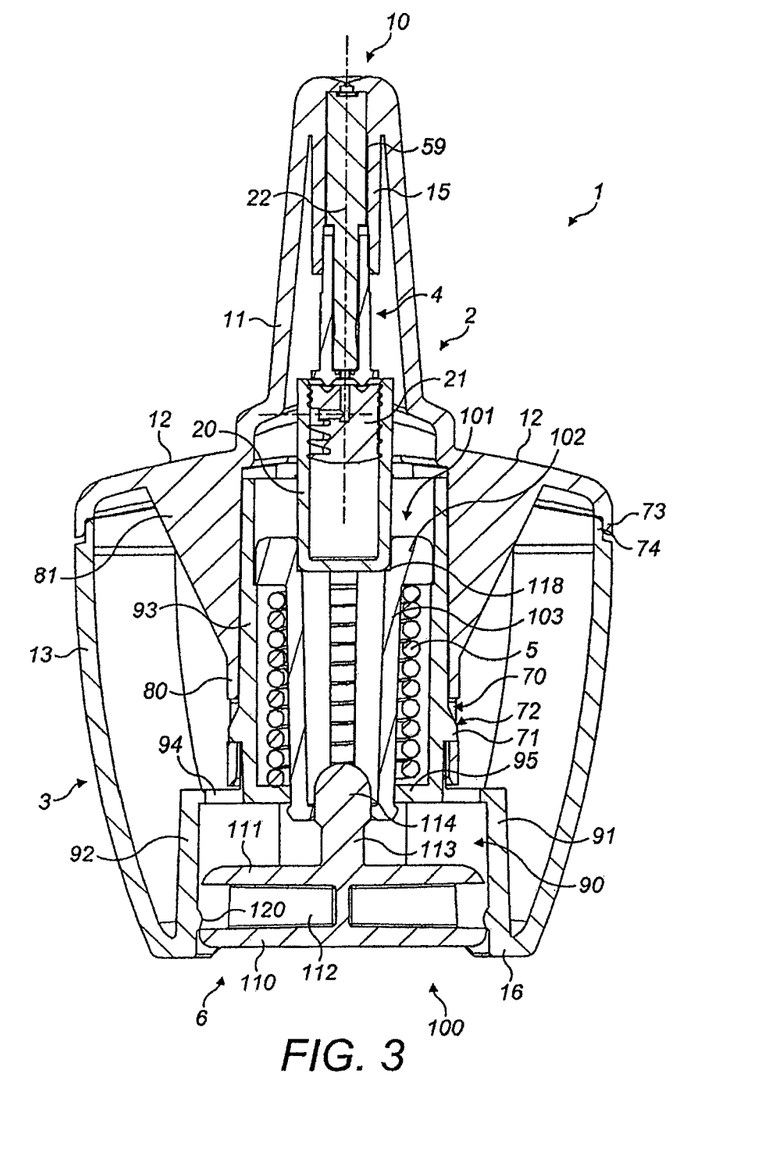
FIG. 3 is a cross-sectional view of the nasal device of FIG. 1.

The housing of the device is formed from two parts, the upper housing 2 and the lower housing 3. The upper housing 2 and lower housing 3 connect together by means of a pair of co-operating formations 70 and 71 as best shown in FIG. 3 which will be described further below. A lower rim 73 of the upper housing 2 and an upper rim 74 of the lower housing 3 interface with one another on assembly of the device 1. An optional additional snap-fit arrangement or ultrasonic weld may be provided at this interface if desired.

The housing defines an interior for containing the remaining components of the device 1. The upper housing 2 and lower housing 3 together define a side wall 13 of the housing, a base 16 and opposite the base a nasal piece 11 which extends upwardly towards an outlet orifice 10 which is provided at a distal end thereof. A longitudinal axis of the device 1 runs from the base 16 to the outlet orifice 10. Shoulder portions 12 are provided between the nasal piece 11 and side wall 13.

As best shown in the cross-sectional view of FIG. 3, the nasal piece 11 is provided with a first tubular extension 15 which extends downwardly from an upper end of the nasal piece 11 towards the interior of the device 1. In addition, a second tubular extension 80 extends downwardly from the shoulders 12 towards the base 16. A plurality of strengthening webs 81 are provided at an upper end of the second tubular extension 80. Towards a lower end of the second tubular extension 80 are located two apertures 70 on opposite sides thereof. The bottom end of the second tubular extension 80 is open.

The base 16 of the device 1 comprises a recess 90 formed by a third upwardly extending tubular extension 91 of the lower housing 3. The third tubular extension 91 has a stepped configuration with a relative wide lower part 92 and a relatively narrow upper part 93 joined together by a flange 95 having an outer portion in which two apertures 94 are provided to allow access by mould tools during manufacture and an inwardly extending portion which defines a central aperture 96. A raised annular ridge 120 is provided on an inner face of the third tubular extension 91.

The trigger mechanism 6 comprises a button 100 and slide 101.

Figure 4:
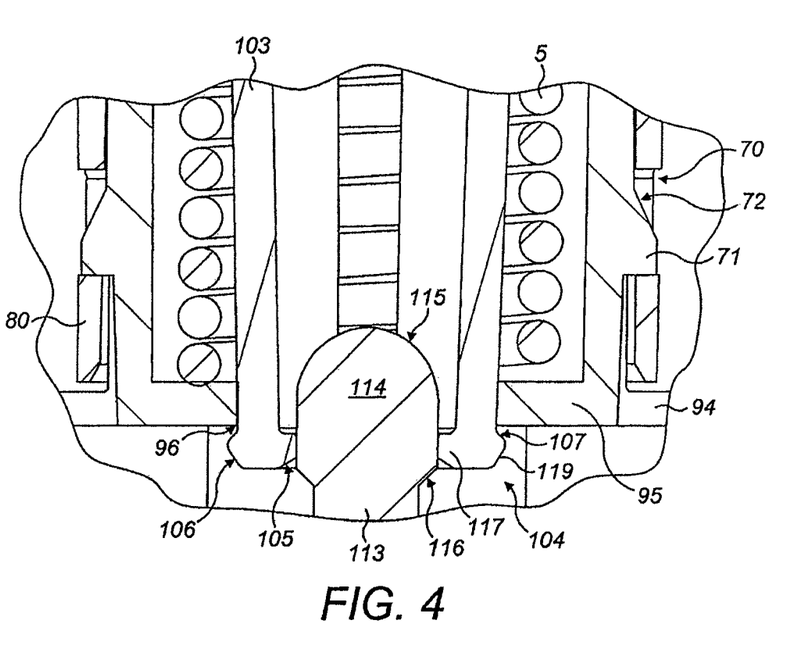
FIG. 4 is an enlarged view of a section of FIG. 3.

The button 100 comprises a body formed from an inner transverse flange 111 and an outer transverse flange 110 joined together by an X-shaped web structure 112. The button 100 is provided with a projection 113 having a relatively slim body that extends inwardly from the inner flange 111 and terminates in an enlarged head 114. As best shown in FIG. 4, the distal end 115 of the head 114 is dome-shaped and an inclined shoulder 116 is formed at the junction between the head 114 and the body of the projection. A lower face of the flange 110 forms a trigger surface that can be contacted in use by a finger or thumb of a user.

The slide 101 comprises a ring portion 102 and three dependent legs 103. The ring portion 102 is annular and has an inwardly directed shoulder 118 at a base of a recess, the use of which will be described below. The legs 103 extend downwards and each terminate in an enlarged catch portion 104. As best shown in FIG. 4, each catch portion 104 comprises an inwardly directed projection 117 and an outwardly directed projection 119. An outer edge of the catch portion 104 is provided with a downward facing chamfer 106. An inner edge of a lower face of the projection 117 is provided with a downward facing chamfer 105. An outer edge of an upper face of the projection 119 is provided with an upward facing chamfer 107.

Figure 5:
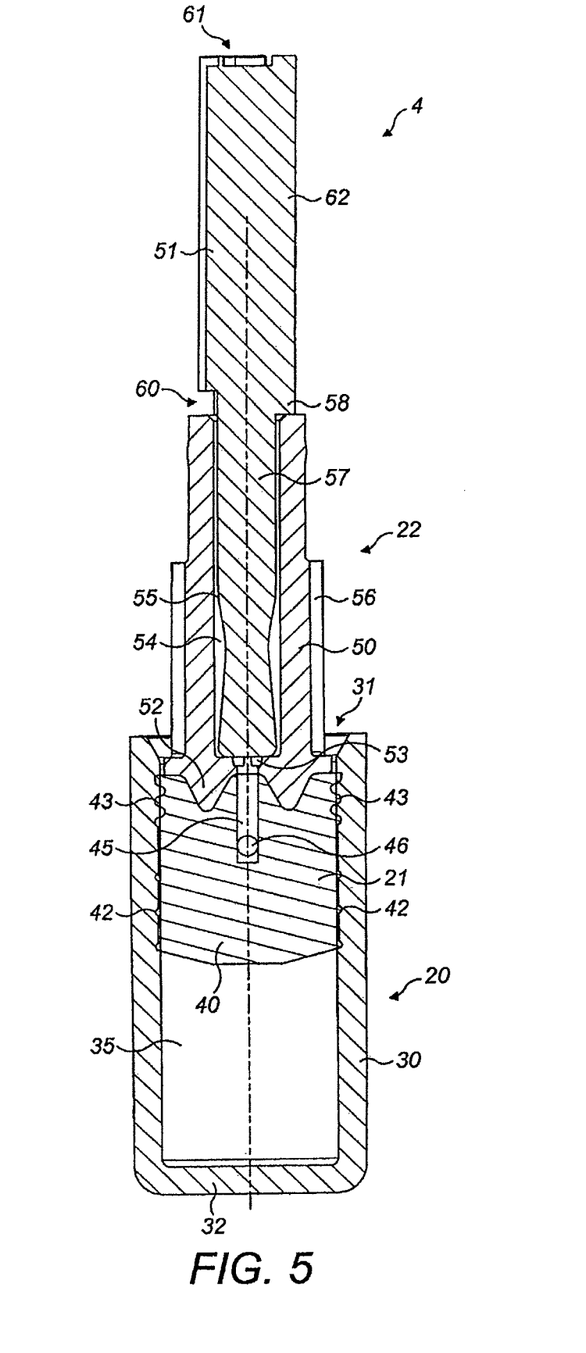
FIG. 5 is a cross-sectional view of a piston pump of the nasal device of FIG. 1.

The piston pump 4 is shown in FIG. 5 and comprises a container 20, a piston 21 and a plunger 22.

The container 20 comprises a generally cylindrical body 30 which has a closed base 32 at one end and an upper opening 31 at an end opposite the base 32. The container 20 defines a pump chamber 35 in which in use a fluid may be stored prior to discharge on operation of the device 1.

Figure 6:
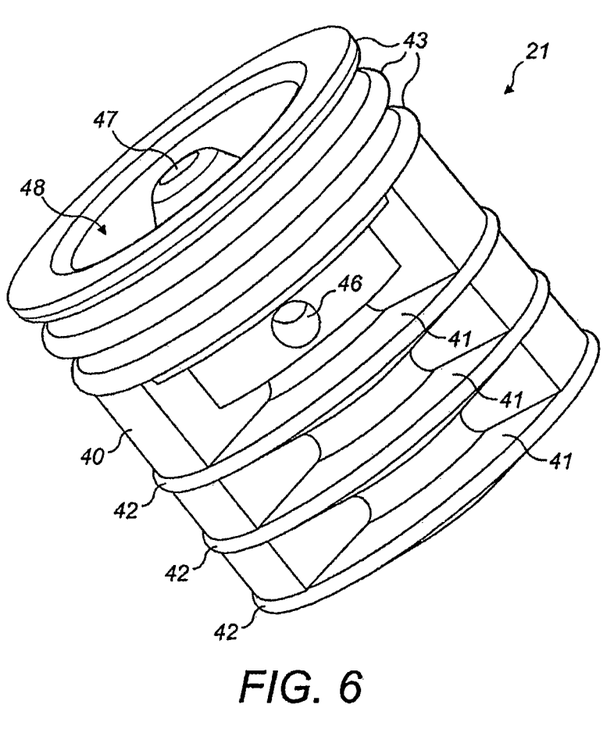
FIG. 6 is a perspective view of a piston of the nasal device of FIG. 1.

The piston 21 comprises a piston body 40 which is shown in more detail in FIG. 6. The piston body 40 is generally cylindrical but is provided with a number of shaped zones and projections for carrying out various functions. Three resilient projections 41 are provided spaced apart axially along the lower half of the piston body 40. Each resilient projection 41 extends circumferentially around a portion of the circumference of the piston body 40. The resilient projections 41 extend through an arc of approximately 100 degrees. The resilient projections 41 are relatively deep in the radial direction and this relatively large radial depth of the projections 41 renders them relatively flexible compared to the other sealing formations described below. The piston body 40 is further provided with three sealing projections 42 which are each axially aligned with one of the resilient projections 41 and are formed as a circumferential extension of the outward radial edge of the resilient projections 41. Each of the sealing projections 42 extend round the remainder of the circumference of the piston body 40 not coincident with the sector of the resilient projections 41. Thus each sealing projection 42 extends round an arc of approximately 260 degrees. The sealing projections 42 extend radially slightly beyond the outer surface of the piston body 40. Since the 'depth' in the radial direction of the sealing projections 42 is relatively small compared to the depth of the resilient projections 41 they are relatively much less flexible.

The piston body 40 further comprises three sealing rings 43 provided at an upper end of the piston body 40 spaced axially apart from one another. In between the sealing rings 43 and the resilient projections 41 is provided an inlet port 46 which, as shown in FIG. 5, communicates with a transverse conduit within the interior of the piston body 40. The transverse conduit in turn communicates with an axially oriented axial conduit 45 which extends upwardly through the upper half of the piston body 40 and terminates at an outlet port 47 as shown in FIG. 6. The use of the inlet port 46 and outlet port 47 will be described further below. The upper face of the piston body 40 is provided with a circumferential recess 48 which is shaped to sealingly mate with the lower face of the plunger 22 as shown in FIG. 5.

The plunger 22 comprises a lower plunger portion 50 and an upper plunger portion 51 which are engaged with one another on assembly. If desired the engagement may be made permanent by use of a snap-fit formation or through welding or other adhesive mechanisms. The lower plunger portion 50 comprises a generally cylindrical tubular component having a centrally extending bore 54. A lower end of the bore 54 communicates with an inlet 53 which is provided at a centre of the lower end face of the plunger 22. The lower face of the lower plunger portion 50 is provided with a circumferential ridge 52 shaped to matingly engage in sealing manner with the circumferential recess 48 of the piston body 40. A plurality of axially extending strengthening ribs 56 extend up a portion of the exterior surface of the lower plunger portion 50 as shown most clearly in FIG. 5.

The upper plunger portion 51 comprises a generally cylindrical component having a narrower plug portion 57 at a lower end and a wider upper portion 62 at an upper end. On assembly as shown in FIG. 3, the plug portion 57 is received within the bore 54 of the lower plunger portion 50 to define a lower portion 55 of a delivery channel which is annular in shape and lies between the internal surface of the lower plunger portion 50 and the exterior surface of the plug portion 57. As shown in FIG. 5, the upper portion 62 is provided with three spacers 58 which abut against an upper edge of the lower plunger portion 50. The spacers 58 act as standoffs to create three radial ports 60 that connect the inner portion 55 of the delivery channel to an upper portion 59 of the delivery channel which is formed, as shown in FIG. 3, between an exterior face of the outer plunger portion 51 and an inner face of the tubular extension 15 of the upper housing 2. This outer portion 59 of the delivery channel comprises three axially extending paths that are defined by grooves formed in the surface of the outer plunger portion 51. Each groove extends from a respective port 60 upwardly to the upper end of the plunger portion 22. A swirl chamber formation 61 is provided at the upper end of the plunger 22.

The device 1 is assembled as follows. The container 20 is filled with a dose of a desired fluid and the piston 21 is inserted. The plunger 22 is inserted into the tubular extension 15 of the upper housing 2 so that the swirl chamber 61 abuts against the outlet orifice 10. The spring 5 and then the slide 101 are inserted through the open upper end of the lower housing 3 into the tubular extension 93. A lower end of the spring 5 comes to rest on the inner portion of the flange 95. As the slide 101 reaches the full insertion point the chamfer 106 on the outer edge of the catch portions 104 contacts the flange 95 causing the legs 103 to deflect towards each other enabling the catch portions 104 to pass through the aperture 96. Once past the flange 95, the legs 103 spring back into there original configuration. When fully inserted the ring portion 102 of the slide 101 has contacted and compressed the spring 5 as shown in FIG. 3. Due to the chamfer 107 on the catch portions 104, the upward biasing force of the spring 5 on the slide 101 has the effect of wanting to pull the catch portions 104 back through the aperture 96. However this is prevented by inserting the button 100 into the tubular extension 92 of the lower housing 3 such that the head 114 is received in the aperture as shown in FIG. 3 at a location where the head 114 contacts the inwardly directed projections 117 which prevents the legs 103 deflecting towards one another. In this position the outer flange 110 is abutted against a lower side of the annular ridge 120 on the tubular projection 92. The button 100 is retained in the cavity 90 by contact between the annular ridge 120 and the inner transverse flange 111.

The container 20 and piston 21 are now inserted into the open upper end of the tubular projection 93 so that a lower end of the container rests against the shoulder 118 of the ring portion 102.

Finally, the upper housing 2 is located over the lower housing such that the tubular portion 93 slides upwards within the tubular portion 80 until the upper housing 2 and lower housing 3 snap-fit together on engagement of the co-operating formations 70, 71. The inclined upper face 72 of the projections 71 enable the tubular projection 80 to flex sufficiently for the parts to be assembled but the flat lower face of the projections 71 prevents the parts thereafter being separated. In this assembled position, the piston 21 is brought into mating contact with the lower end of the plunger 22 as shown in FIG. 3.

The fluid in the chamber 35 comprises a single dose of fluid to be discharged. Typically, the fluid contains a pharmaceutical. The pharmaceutical may be provided as a solution or powder suspension in a solvent or carrier liquid, for example ethanol, or isopropyl alcohol.

The device 1 is shown in FIG. 3 with a trigger mechanism (formed from the button 100 and the flexible legs 103 of the slide 101) in a cocked configuration in which a biasing mechanism (formed from the combination of the spring 5 and the slide 101) is unable to transfer its biasing force to the casing 20 so as to move the casing 20 upwardly.

To use the device 1, a user grips the device 1 between the base 16 and the shoulder portions 12 and places the nasal piece 11 into a nostril. With a single finger or thumb the device 1 is moved into a triggered configuration by pushing up on the trigger surface of button 100. With sufficient pressure the transverse outer flange 110 is flexed and pushed past the annular ridge 120 such that the enlarged head 114 moves upwards and out of alignment with the catch portions 104. Once the thinner body of the projection 113 is aligned with the catch portions 104 the legs 103 can flex together under the force of the spring 5 pushing up on the ring portion 102 and the inclined contact between the chamfers 107 of the catch portions 104 riding over the inner edge of the aperture 96. Thus movement of the button 100 causes the slide 101 to be decoupled from the lower housing 3 and as a result the slide 101 moves rapidly upwards under the force of spring 5 pushing the body 30 of the container 20 with it.

Due to the fact that the plunger 22 and piston 21 are fixed axially relative to the upper housing 2, the upward movement of the body 30 of the container 20 has the corresponding effect of trying to reduce the volume of the pump chamber 35 which results in pressurisation of the fluid within the pump chamber 35. This increase in the pressure of the fluid within the pump chamber 35 causes the resilient projections 41 to deflect upwards allowing passage of the pressurised fluid between the resilient projections 41 and the inner face of the body 30 of the container 20. Thus, the pressurised fluid is enabled to reach the inlet port 46 of the piston body 40. The passage of fluid is only enabled through the 100 degree sector where the resilient projections 41 are located due to the relatively stiffer sealing performance of the sealing projections 42 around the remainder of the circumference of the piston body 40. In addition, pressurised fluid cannot escape fully out of the pump chamber 35 other than via inlet port 46 due to the higher sealing performance of the sealing rings 43.

Thus, pressurised fluid exits the pump chamber 35 through inlet port 46, along transverse conduit, along axial conduit 45 and out of outlet port 47 of the piston body 40. Due to the fact that the outlet port 47 of the piston body 40 is aligned with the inlet 53 of the plunger 22, the pressurised fluid enters the lower portion 55 of the delivery channel and is discharged upwardly between the lower plunger portion 50 and the plug portion 57 of the upper plunger portion 50. Thereafter, the pressurised fluid passes through the ports 60 into the upper portion 59 of the delivery channel between the upper portion 62 and the tubular extension 15. Finally, the pressurised fluid reaches the swirl chamber formation 61 where the fluid is forced into a rotational swirl pattern before exiting the outlet orifice 10 in the form of a spray.

The device 1 is preferably a disposable, single use device.

Figure 7:
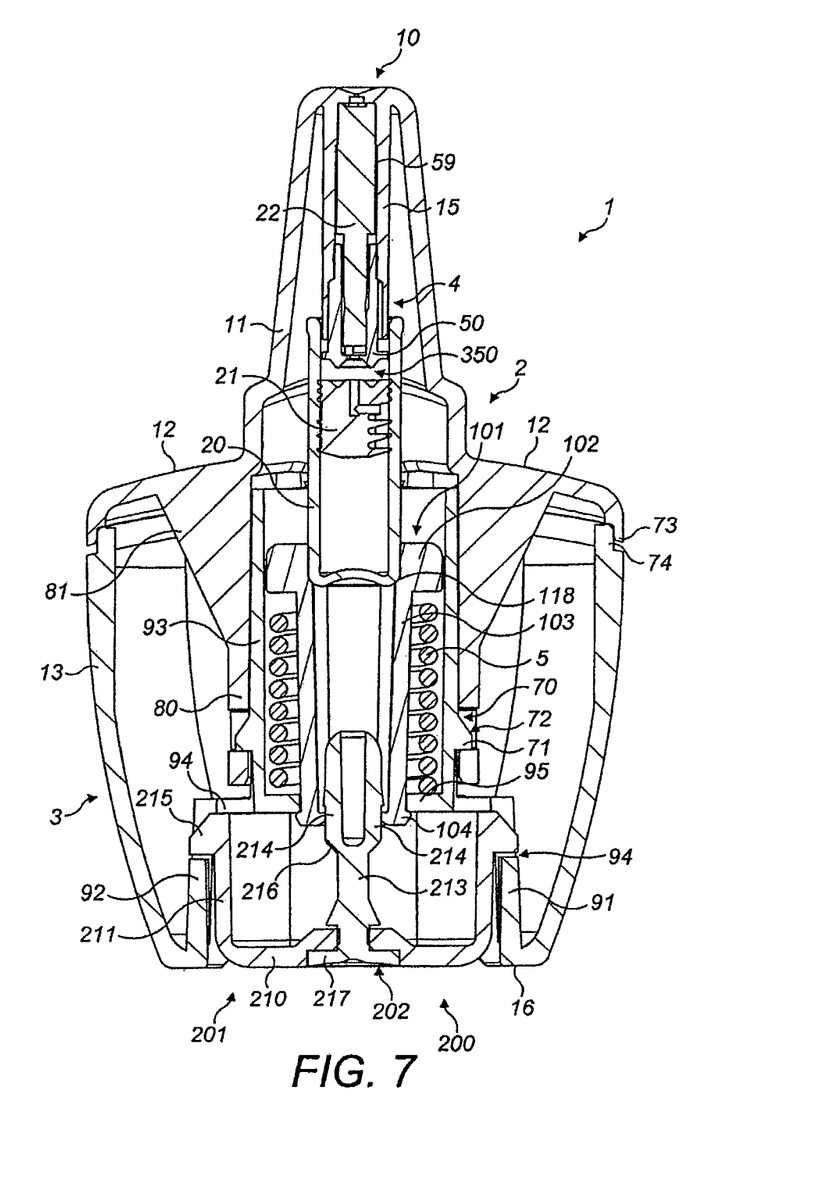
FIG. 7 is a cross-sectional view of a second nasal device as described in WO2013/054076.

The second nasal device is shown in FIG. 7. In the following, only those differences between this device and the preceding device will be described. In all other aspects, the device 1 is of the same form and functions in the same manner as the first device. Consequently, like reference numerals are used in the Figures for like parts.

The button 200 of the second device 1 differs from the first device. The button 200 comprises two parts, a cup-shaped body 201 and a projecting part.

The body 201 comprises a bottom 210 and a lateral side wall 211. The side wall 211 is provided with projections 215 at its distal end which engage with the apertures 94 of the tubular extension 91. The bottom 210 is provided with an aperture 202 in which is located the projecting part. The body 201 does not comprise an equivalent to the inner flange 111 of the first device.

The projecting part comprises a relatively slim body 213 that extends inwardly from the bottom 210 and terminates in an enlarged head 214. The distal end of the head 214 is dome-shaped and an inclined shoulder 216 is formed at the junction between the head 214 and the body of the projection.

A lower face of the bottom 210 forms a trigger surface that can be contacted in use by a finger or thumb of a user. Preferably, the trigger surface may also comprise a flange 217 of the projecting part.

Preferably, the body 201 is formed from a thermoplastic elastomer (TPE) or other suitably flexible, resilient material. The projecting part is formed from a relatively rigid material such as polypropylene (PP). The body 201 and projecting part may be connected in any suitable manner although a preferred option is to form the button as a comoulding.

The body 201 is flexible to allow movement of the projecting part without disconnection of the body 201 from the tubular extension 91 or disengagement of the projections 215 from the apertures 94. Movement of the projecting part is accommodated by deflection or deformation of the side wall 211 and/or bottom 210, for example by folding, bending or stretching of the material.

In use, the device 1 is moved from the cocked configuration of FIG. 7 into the triggered configuration by pushing up on the trigger surface of button 200, causing the projecting part to move upwards. The body 201 flexes to accommodate the upwards movement of the projecting part. As the projecting part 213 moves upwards, the enlarged head 214 also moves upwards and eventually out of alignment with the catch portions 104. Once the thinner body 213 of the projecting part is aligned with the catch portions 104 the legs 103 can flex together under the force of the spring 5 pushing up on the ring portion 102 and the inclined contact between the chamfers 107 of the catch portions 104 riding over the inner edge of the aperture 96. Thus movement of the projecting part causes the slide 101 to be decoupled from the lower housing 3 and as a result the slide 101 moves rapidly upwards under the force of spring 5 pushing the body 30 of the container 20 with in the same manner as described with reference to the first device.

The use of the resilient button 200 reduces the noise produced during operation of the device, in particular because the button 200 does not comprise an inner flange that is brought forcefully into contact with the flange 95 of the housing.

Figure 8:
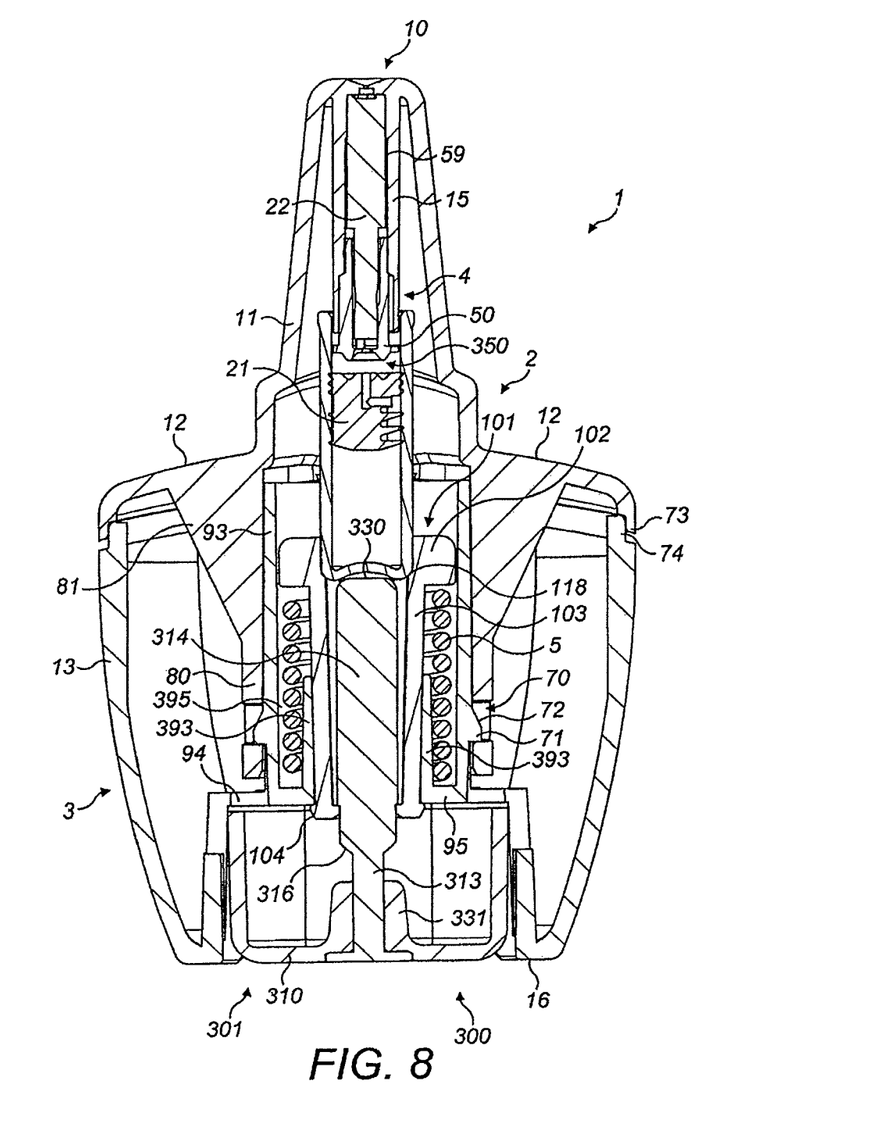
FIG. 8 is a cross-sectional view of a third nasal device as described in WO2013/054076.

The first and second devices 1 may comprise assembly gaps between components. Examples are a gap 350 which may be present between the lower plunger portion 50 and the piston 21 and a gap (not shown) between the container 20 and the slide 101. These assembly gaps can be advantageous to ensure that during manufacture and assembly of the device the piston 21 is not inadvertently moved within the casing 20 which could lead to premature leakage of product. The presence of the gaps thus eases manufacture and assembly. However, during actuation of the device 1 the assembly gaps are rapidly closed during movement of the components under the force of the biasing spring. The resulting impacts between the components may result in the generation of noise which may be undesirable for the user. The third device 1 as shown in FIG. 8 seeks to overcome this potential disadvantage.

In the following, only those differences between the third device and the second device will be described. In all other aspects, the device 1 is of the same form and functions in the same manner as the second device. Consequently, like reference numerals are used in the Figures for like parts.

The button 300 comprises two parts, a cup-shaped body 301 and a projecting part.

As before, the body 301 comprises a bottom 310 and a lateral side wall and is substantially the same and formed from the same materials as in the second device. Two variations may be noted. Firstly, the side wall is not provided with projections at its distal end. Secondly, an enlarged mount 331 is provided for the projecting part to create a stronger connection between the body 301 and the projecting part. As before, the parts are preferably comoulded together.

The relatively slim body 313 of the projecting part is substantially as before. However the enlarged head 314 is significantly elongated such that it extends up and into the immediate vicinity of the bottom of the casing 20. Only a small assembly gap 330 may be provided therebetween if desired.

An inclined shoulder 316 is again formed at the junction between the head 314 and the body of the projecting part.

The housing is also modified in the vicinity of the spring 5 by providing an inner tubular extension 393 inside the tubular extension 93 which creates an annular chamber 395 therebetween. The inner tubular extension extends upwardly from the flange 95 which closes of the lower end of the annular chamber 395. The spring 5 is located within the annular chamber 395.

In use, the device 1 is moved from the cocked configuration of FIG. 8 into the triggered configuration by manually pushing up on the trigger surface of button 300, causing the projecting part to move upwards. The body 301 flexes to accommodate the upwards movement of the projecting part.

The initial upward movement of the projecting part 313 causes the distal end of the enlarged head 314 to contact the lower end of the casing 20 by closing the assembly gap 330 (if present). Next the upward movement moves the casing 20 and piston 21 (as one) upwards to bring the piston 21 into contact with the lower plunger portion 50, thus closing the assembly gap 350. It should be noted that the assembly gaps are closed during the relatively slow manual movement of the button 300. Therefore no, or little, noise is produced during this stage.

As the projecting part is moved manually further upwards, the enlarged head 314 also moves upwards and eventually out of alignment with the catch portions 104 as before. Once the thinner body 313 of the projecting part is aligned with the catch portions 104 the legs 103 can flex together under the force of the spring 5 to engage the projecting part under the shoulder 316. At this point the slide 101 is decoupled from the lower housing 3 and as a result the slide 101 can move rapidly upwards under the force of spring 5. During this movement the legs 103 are constrained to remain inwardly flexed due to the internal diameter of the inner tubular extension 393 against which the catch portions 104 slide. Consequently, the biasing force of the spring 5 acting on the slide 101 is transferred via the catch portions 104 and the shoulder 316 to the projecting part of the button 300. Thus, the biasing force is applied to the casing 20 via the enlarged head 314 of the button 300 and not via just the slide 101. Since the assembly gaps of the device are closed prior to the slide 101 being decoupled, the activation noise is significantly reduced. Activation noise is also reduced by the presence of the inner tubular extension 393 as it helps to prevent recoil and 'snaking' of the spring 5 which may occur where a larger void space is provided surrounding the spring.

The third device 1 is configured such that the slide 101 moves a predetermined actuation distance on actuation of the device. The inner tubular extension 393 has a length equal to or greater than this actuation distance. As a result, after actuation, the legs 103 are retained within the bore of the inner tubular extension with the catch members still engaged under the shoulder 316. This prevents the button 300 moving back downwards. This is advantageous in that it acts as a visible indicator that the device has been actuated and provides a stable post-actuation structure in which the components are not free to be rattled about.

While the description of the third device above describes the enlarged elongate head 314 directly contacting the container 20, it will be appreciated that the closure of the assembly gaps may also be achieved by indirect contact through an intermediate component between the projecting part and the casing 20. For example, the elongate head 314 may be formed from two or more pieces that are moved in turn.

Figure 9:
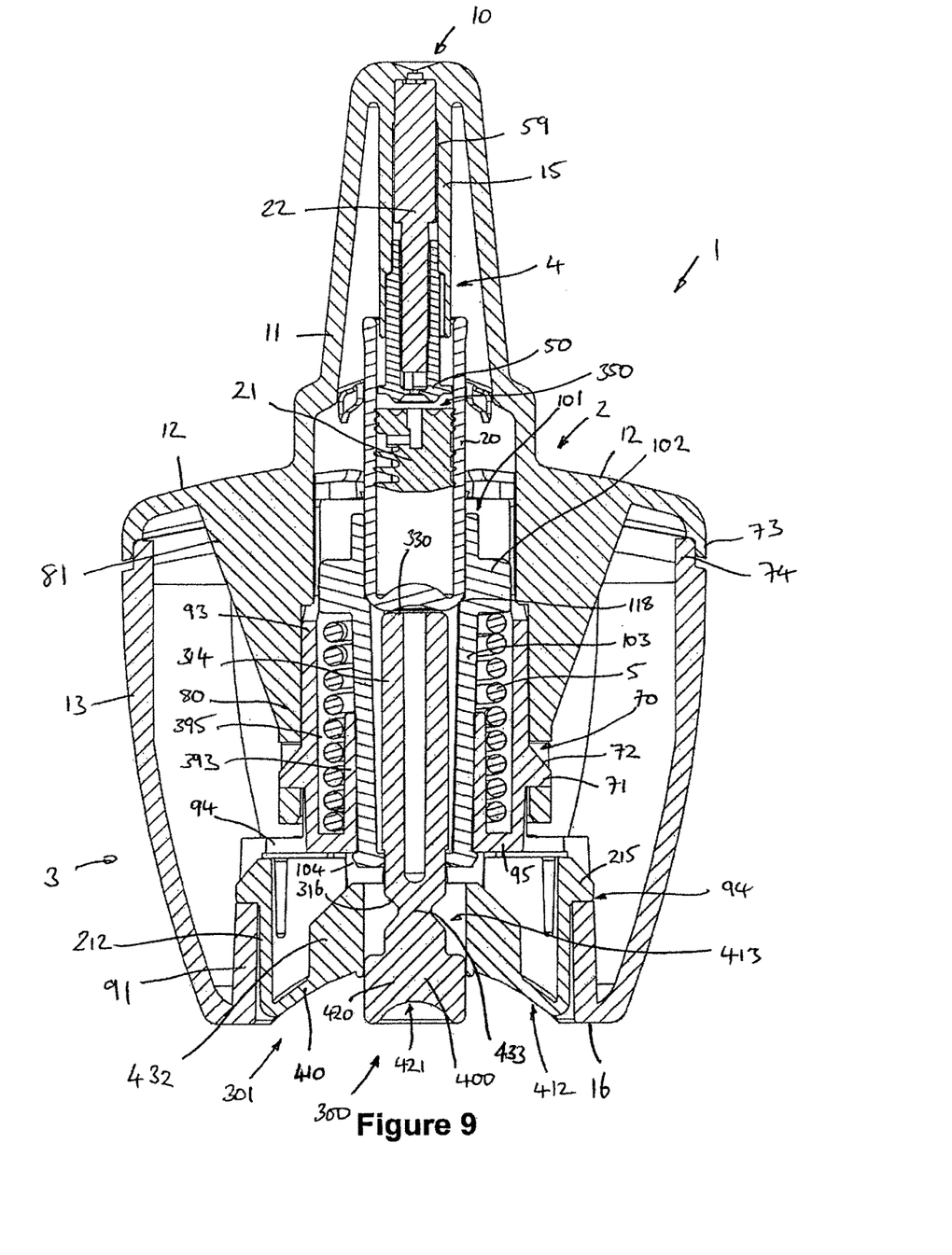
FIG. 9 is a cross-sectional view of a fourth nasal device according to the present disclosure.
Figure 10:
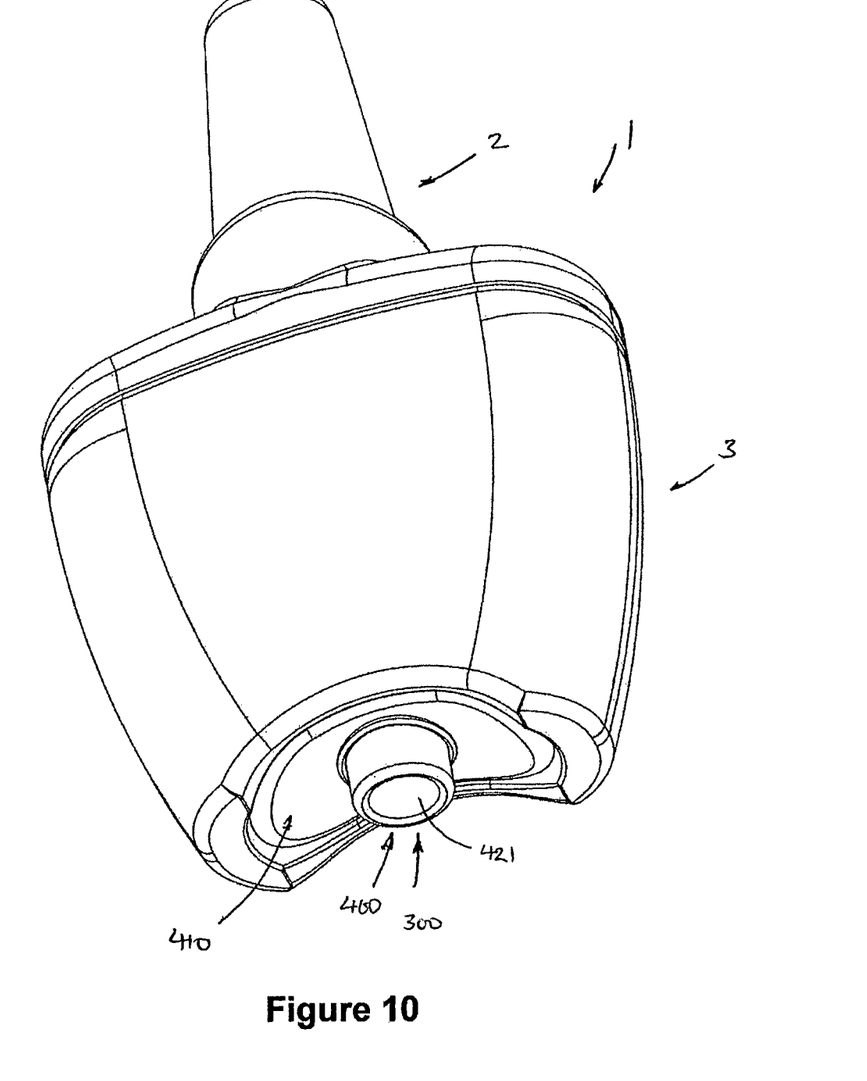
FIG. 10 is a perspective view of the nasal device of FIG. 9.

FIGS. 9 and 10 illustrate a fourth device according to the present disclosure. In the following, only those differences between the fourth device and the third device will be described in detail. In all other aspects, the device is of the same form and functions in the same manner as the third device. Consequently, like reference numerals are used in the Figures for like parts.

In this device, the button 300 comprises a central, slidable button 400 which moves relative to a shroud 410, which preferably remains stationary during use.

The shroud 410 comprises a cup-shaped body 301 having an outer lateral side wall 212 and a concave lower end 412. In addition, the shroud 410 is provided with an inner tubular section 432 extending upwardly from the lower end 412 and defining a central conduit 413 extending upwardly from an aperture in the concave lower end 412. The lower end 412 closes off the shroud 410 between the outer lateral side wall 212 and the aperture. An upper end of the outer lateral side wall 212 is provided with projections 215 which, as described before, engage with the apertures 94 of the tubular extension 91 to retain the shroud 410 with respect to the lower housing 3.

The slidable button 400 comprises a relatively stubby lower end 420 provided with a concave lower face 421. The lower end 420 is connected to the enlarged head 314 by means of a waisted section 433. Compared to the third device, the waisted section 433 is shorter in axial length than the projecting part 313 but is still provided with an inclined shoulder 316 formed at the junction between the enlarged head 314 and the waisted section 433. The diameter of the lower end 420 forms a sliding fit in the conduit 413 of the shroud 410. In the cocked configuration of FIG. 9 the lower end 420 projects outside the shroud 410 such that the concave lower surface 421 is easily accessible for triggering by the thumb or finger of a user.

As before, the enlarged head 314 extends up and into the immediate vicinity of the bottom of the casing 20. Only a small assembly gap 330 may be provided therebetween if desired. In this device, the enlarged head 314 is shown as hollow. A solid enlarged head may be used as an alternative.

As in the third device, the lower housing 3 is provided with an inner tubular extension 393 inside the tubular extension 93 which creates an annular chamber 395 therebetween. The inner tubular extension extends upwardly from the flange 95 which closes of the lower end of the annular chamber 395. The spring 5 is located within the annular chamber 395.

The respective parts of the fourth device may be formed from the same materials as in the above devices.

In use, the device 1 is moved from the cocked configuration of FIG. 9 into the triggered configuration by manually pushing up on the concave lower surface 421 of button 300, causing the whole of the slidable button 400 to move upwards relative to the shroud 410.

The initial upward movement of the slidable button 400 causes the distal end of the enlarged head 314 to contact the lower end of the casing 20 by closing the assembly gap 330 (if present). Next the upward movement moves the casing 20 and piston 21 (as one) to move upwards to bring the piston 21 into contact with the lower plunger portion 50, thus closing the assembly gap 350. It should be noted that the assembly gaps are closed during the relatively slow manual movement of the slidable button 400. Therefore no, or little, noise is produced during this stage.

As the slidable button 400 is moved manually further upwards, the enlarged head 314 also moves upwards and eventually out of alignment with the catch portions 104 as before. Once the waisted section 433 of the slidable button 400 is aligned with the catch portions 104 the legs 103 can flex together under the force of the spring 5 to engage the projecting part under the shoulders 316. At this point the slide 101 is decoupled from the lower housing 3 and as a result the slide 101 can move rapidly upwards under the force of spring 5. During this movement the legs 103 are constrained to remain inwardly flexed due to the internal diameter of the inner tubular extension 393 against which the catch portions 104 slide. Consequently, the biasing force of the spring 5 acting on the slide 101 is transferred via the catch portions 104 and the shoulder 316 to the slidable button 400. Thus, the biasing force is applied to the casing 20 via the enlarged head 314 of the slidable button 400 and not via just the slide 101. Consequently, the slidable button 400 as a whole is moved upwardly within the device so that the lower end 420 is fully recessed within the conduit 413 and the lower concave surface 421 of the button 400 is recessed relative to the concave lower part 412 of the shroud 410.

Since the assembly gaps of the device are closed prior to the slide 101 being decoupled, the activation noise is significantly reduced. Activation noise is also reduced by the presence of the inner tubular extension 393 as it helps to prevent recoil and 'snaking' of the spring 5 which may occur where a larger void space is provided surrounding the spring.

The fourth device 1 is configured such that the slide 101 moves a predetermined actuation distance on actuation of the device. The inner tubular extension 393 has a length equal to or greater than this actuation distance. As a result, after actuation, the legs 103 are retained within the bore of the inner tubular extension with the catch members still engaged under the shoulder 316. This prevents the slidable button 400 moving back downwards to project beyond the lower concave part 412. This is advantageous in that the recessed location of the actuator button 400 acts as a visual and tactile indicator that the device has been activated. In addition it provides a stable post-actuation structure in which the components are not free to be rattled about.

While the description of the fourth device above describes the enlarged elongate head 314 directly contacting the container 20, it will be appreciated that the closure of the assembly gaps may also be achieved by indirect contact through an intermediate component between the projecting part and the casing 20. For example, the elongate head 314 may be formed from two or more pieces that are moved in turn.

The invention claimed is:

1. A fluid delivery device for discharging a fluid comprising:
   a housing;
   a piston pump;
   a biasing mechanism; and
   a trigger mechanism;
   the housing comprising a basal end and a discharge end having an outlet for discharging the fluid;
   the piston pump comprising a casing defining a pump chamber for storage of the fluid, a piston slidably movable relative to the pump chamber, a piston plunger, and a delivery channel for delivering fluid discharged from the pump chamber to the outlet of the housing;
   the trigger mechanism being movable from a cocked configuration to a triggered configuration;
   in the cocked configuration the trigger mechanism prevents transfer of a biasing force of the biasing mechanism to the casing to thereby prevent movement of the casing towards the outlet of the housing;
   in the triggered configuration the trigger mechanism enables transfer of the biasing force to the casing to thereby cause movement of the casing towards the outlet of the housing so as to discharge fluid from the pump chamber, along the delivery channel and out of the outlet of the housing;
   the biasing mechanism comprising one or more flexible catch members which in the cocked configuration are catched to the housing and in the triggered configuration are decoupled from the housing; and wherein the trigger mechanism comprises a manually operable trigger located at the basal end of the housing, the manually operable trigger comprising a shroud and a slidable button;
   the slidable button comprising an obstructer that in the cocked configuration engages the one or more flexible catch members to prevent decoupling of the one or more catch members from the housing;
   wherein in the cocked configuration the slidable button projects outside the shroud so as to be accessible, and wherein in the triggered configuration the slidable button is retained within the shroud to provide a visual and tactile activation indicator.

2. A fluid delivery device as claimed in claim 1 wherein the shroud comprises a cup-shaped body having an outer lateral side wall and a concave lower end.

3. A fluid delivery device as claimed in claim 2 wherein the shroud further comprises an inner tubular section extending upwardly from the concave lower end to define a central conduit extending upwardly from an aperture in the concave lower end.

4. A fluid delivery device as claimed in claim 2 wherein an upper end of the outer lateral side wall comprises projections which engage with the housing to retain the shroud with respect to the housing.

5. A fluid delivery device as claimed in claim 1 wherein the slidable button comprises a concave lower face.

6. A fluid delivery device as claimed in claim 1 wherein the one or more catch members and the housing comprise inter-engaging surfaces that in the cocked configuration urge the catch members to flex and decouple from the housing, wherein the position of obstructer in the cocked configuration prevents said flexure.

7. A fluid delivery device as claimed in claim 6 wherein the inter-engaging surfaces comprise inclined surfaces on the catch members.

8. A fluid delivery device as claimed in claim 1 wherein the slidable button comprises, or is coupled to, an inwardly directed projection comprising an enlarged head at a distal end, wherein the enlarged head comprises the obstructer.

9. A fluid delivery device as claimed in claim 8 wherein the one or more flexible catch members comprises a plurality of flexible legs depending from a body portion, each flexible leg comprising a catch portion at a distal end.

10. A fluid delivery device as claimed in claim 9 wherein in the cocked configuration the catch portions are located around the enlarged head of the obstructor and axially aligned therewith.

11. A fluid delivery device as claimed in claim 10 wherein the slidable button comprises, or is coupled to, a waisted section below the obstructer and the slidable button is movable into the triggered configuration by movement away from the basal end into the housing so as to slide the enlarged head of the obstructor within the flexible legs to bring the waisted section into alignment with the catch portions.

12. A fluid delivery device as claimed in claim 1 further comprising a slide member which comprises the one or more flexible catch members.

13. A fluid delivery device as claimed in claim 12 wherein the slide member comprises a recess for receiving and, optionally, abutting against the casing.

14. A fluid delivery device as claimed in claim 12 wherein the slide member is configured, in the triggered configuration, to transfer the biasing force to the casing of the piston pump.

15. A fluid delivery device as claimed in claim 14 wherein the slide member transfers the biasing force to the casing by direct contact therebetween.

16. A fluid delivery device as claimed in claim 1 wherein the obstructor is configured, in the triggered configuration, to transfer the biasing force to the casing of the piston pump.

17. A fluid delivery device as claimed in claim 16 wherein the obstructor transfers the biasing force to the casing by direct contact therebetween.

18. The fluid delivery device of claim 1 wherein the device is a single-use device.

19. A dose containing fluid delivery device; comprising the fluid delivery device of claim 1 combined with a single dose of fluid contained in the pump chamber.

20. The fluid delivery device of claim 1 wherein the fluid delivery device is one selected from the group consisting of a nasal fluid delivery device, a sub-lingual fluid delivery device, and an ophthalmic use fluid delivery device.

* * * * *